United States Patent [19]

Hall

[11] 4,172,058
[45] Oct. 23, 1979

[54] CHEMICAL PROCESS AND SUBSTANCE FOR INHIBITION OF FLUID EVAPORATION

[76] Inventor: J. Marion Hall, P.O. Box 444, Oakland, Ill. 61943

[21] Appl. No.: 653,600

[22] Filed: Jan. 29, 1976

[51] Int. Cl.² ............................................. C08L 3/02
[52] U.S. Cl. ................................ 260/17.4 GC; 47/9; 47/57.6; 47/DIG. 7; 47/DIG. 10; 47/DIG. 11
[58] Field of Search ............... 260/17.4 GC; 47/57.6, 47/9, DIG. 7–DIG. 11

[56] References Cited

U.S. PATENT DOCUMENTS 3,935,099  1/1976  Weaver et al. ..................... 260/17.4

OTHER PUBLICATIONS

Chem. Abstrs., vol. 71, 53887s, "Effect of Higher Fatty Alcohols on the Evaporation Rate of Water at Low Temperatures," Chalenko.
Chem. Abstrs., vol. 73, 112746m, "Influence-Reduction of Water Vapor-1-Octadecanol-Monolayers," Krmoyan et al.

Primary Examiner—Edward M. Woodberry
Attorney, Agent, or Firm—Rogers, Eilers & Howell

[57] ABSTRACT

The admixing of highly absorbent starch-containing polymeric compositions with higher fatty alcohols containing 12 carbon atoms per molecule to 24 carbon atoms per molecule, thereby reducing and/or inhibiting the evaporation of fluid from the highly absorbent starch-containing polymeric compositions.

12 Claims, No Drawings

CHEMICAL PROCESS AND SUBSTANCE FOR INHIBITION OF FLUID EVAPORATION

PRIOR ART

Prior art patents include U.S. Pat. No. 3,935,099, issued Jan. 27, 1976 to Agricultural Research Service, U.S.D.A. for "Highly Absorbent Starch-Containing Polymeric Compositions"; and U.S. Pat. No. 3,205,059, to Roberts, issued Sept. 7, 1965 for "Method of Reducing Transpiration in Plants"; each of said patents being hereby incorporated by reference.

DESCRIPTION OF PREFERRED EMBODIMENT

I know of no previous efforts related specifically to reducing the rate of evaporation of fluids from highly absorbent starch-containing polymeric compositions.

This invention relates to evaporation of fluids from highly absorbent starch-containing polymeric compositions.

This invention relates to the method of inhibiting evaporation of fluids from highly absorbent starch-containing polymeric compositions which comprises mixing higher fatty alcohols with highly absorbent starch-containing polymeric composition in any ratio, whereby said higher fatty alcohol seeks the air fluid interface of the fluid absorbed by the highly absorbent starch-containing polymeric compositions and inhibits the evaporation of said fluid.

Specifically this invention relates to a method of reducing the rate of evaporation from highly absorbent starch-containing polymeric compositions.

More specifically my invention relates to the reduction of evaporation from starch-polyacrylonitrile graft copolymers.

Further, my invention comprises admixing with the highly absorbent starch-containing polymeric compositions, higher fatty alcohol, containing from 12 carbon atoms to 24 carbon atoms per molecule or a mixture thereof. These higher fatty alcohols seek the air-fluid interface and impede the evaporation of the fluid that has been absorbed by the highly absorbent starch-containing polymeric compositions.

The higher fatty alcohols may be admixed with the highly absorbent starch-containing polymeric compositions by any method. Further, that these higher fatty alcohols may be mixed with any solvent, emulsifying agent or premixed solution that is suitable, before being mixed with the highly absorbent starch-containing polymeric compositions. Further, that the higher fatty alcohols may be mixed with the highly absorbent starch-containing polymeric compositions in a dry or partially dry condition.

The ratio at which the higher fatty alcohol is mixed with the highly absorbent starch-containing polymeric composition will vary with the rate at which the highly absorbent starch-containing composition is to release to the atmosphere the fluids it has absorbed. It is believed that the higher fatty alcohol seeks the air fluid interface of the fluid absorbed by the highly absorbent starch-containing polymeric compositions and inhibits the evaporation of said fluid.

Further, that the ratio at which the higher fatty alcohol is mixed with the highly absorbent starch-containing composition, will vary with the volume of fluid the composition is to absorb.

As a result of my invention the length of time the highly absorbent starch-containing polymeric compositions will retain a portion of the fluids they absorb is greatly increased. This reduction in evaporation makes the use of the compositions resulting from my invention much more applicable in many areas.

More specifically the use of my invention makes highly absorbent starch-containing polymeric compositions more useful in applications such as;

Incorporation of the compositions in porous soils to help the soils retain moisture.

Uses of the compositions in humidity control by regulating evaporation, thus regulating humidity.

Cloud seeding applications, by enabling the compositions to retain their moisture until the moisture absorbed reaches the earth's surface.

My invention opens new areas in seed coating. My invention reduces the rate of evaporation from the compositions when these compositions are used to coat seeds, thus accelerating germination.

My invention is further illustrated by the following examples:

EXAMPLE 1

1.23 ml of H-SPAN (Hydrolyzed Starch-Polyacrylonitrile graft copolymer) was deposited in aluminum cups. To this was added 14.79 ml of tap water. At the end of 24 hours this composition was completely dehydrated.

0.61 ml of H-SPAN was mixed with 0.61 ml of a mixture of 35% hexadecanol and 65% octadecanol. To this mixture was added 14.79 ml of tap water. At the end of 48 hours the sample still retained 5% of the water that was added.

EXAMPLE 2

Five samples were mixed of dry H-SPAN and a dry mixture of 35% hexadecanol and 65% octadecanol. The following ratios were used:

| Sample 1 | 1 part H-SPAN and | 1 part Octa-Hexadeconal |
| Sample 2 | 1 part H-SPAN and | 2 part Octa-Hexadecanal |
| Sample 3 | 1 part H-SPAN and | 3 part Octa-Hexadecanal |
| Sample 4 | 1 part H-SPAN and | 4 part Octa-Hexadecanal |
| Sample 5 | 1 part H-SPAN and | 5 part Octa-Hexadecanal |

From the samples a 1 tenth gram specimen of each was deposited in shallow plastic cups. A 1 tenth gram specimen of H-SPAN was also placed in a like cup. 2.5 ml of tap water was added to each specimen. The specimens were exposed to an environment of 75° F. and 18% relative humidity. The following table shows the results.

The 1 tenth gram specimen of octa-hexadecanol was completely dehydrated at the end of 29 hours.

| Samples | Completely dehydrated | Hours |
|---|---|---|
| 1 | " | 36 hrs. 20 min. |
| 2 | " | 36 hrs. 10 min. |
| 3 | " | 36 hrs. |
| 4 | " | 35 hrs. 10 min. |
| 5 | " | 34 hrs. |

Conclusion: The 1 to 1 mixture, ½ the volume of H-SPAN, when mixed with octa-hexadecanol, my invention, held the moisture 7 hours and 20 minutes longer than the raw specimen of H-SPAN held it's moisture.

Having described my invention and certain embodiments thereof, I claim:

1. The process of inhibiting evaporation of fluids from highly absorbent starch-containing polyacrylonitrile graft copolymer, which comprises mixing a higher fatty alcohol of about 12–24 carbon atoms per molecule with said starch-polyacrylonitrile graft copolymer, whereby evaporation of fluid is inhibited.

2. The process according to claim 1 wherein said higher fatty alcohol contains 16–18 carbon atoms per molecule.

3. The process according to claim 1 wherein said higher fatty alcohol is applied as an admixture of said higher fatty alcohol, an emulsifying agent, a plant nutrient and an inert carrier.

4. The process according to claim 1 wherein said higher fatty alcohol is applied as an admixture of said higher fatty alcohol, an emulsifying agent, a fungicide and an inert carrier.

5. The process according to claim 1 whereby the higher fatty alcohol is applied and admixed with highly absorbent starch-containing polymeric compositions, dry or partially dry.

6. A process as recited in claim 1, further comprising the step of coating seeds with the mixture of higher fatty alcohol and highly absorbent starch-polyacrylonitrile graft copolymer.

7. A process as recited in claim 1 further comprising the step of incorporation of the mixture of higher fatty alcohol with the highly absorbent starch-polyacrylonitrile graft copolymer in soil to aid in soil retention of moisture.

8. A process as recited in claim 1 further comprising the step of using the mixture of higher fatty alcohol with the highly absorbent starch-polyacrylonitrile graft copolymer in humidity control to regulate evaporation.

9. A process as recited in claim 1 further comprising the step of using the mixture of higher fatty alcohol with the highly absorbent starch-polyacrylonitrile graft copolymer by applying the mixture to cloud seeding compositions.

10. A process of inhibiting evaporation of water from a starch-polyacrylonitrile graft copolymer comprising mixing said copolymer with a composition selected from the group consisting of alcohols containing 12–24 carbon atoms per molecule.

11. A water-absorbing evaporation inhibiting composition comprising a highly absorbent starch-polyacrylonitrile graft copolymer composition mixed with a higher fatty alcohol of about 12–24 carbon atoms per molecule.

12. The composition of claim 11 wherein the alcohol is selected from the group consisting of alcohols having 16–18 carbon atoms per molecule.

* * * * *